United States Patent [19]
Grabenkort

[11] Patent Number: 5,915,427
[45] Date of Patent: Jun. 29, 1999

[54] ANESTHETIC VAPORIZER DRAINING SYSTEM

[75] Inventor: Richard W. Grabenkort, Barrington, Ill.

[73] Assignee: Abbott Laboratories, Abbott Park, Ill.

[21] Appl. No.: 08/763,914

[22] Filed: Dec. 11, 1996

[51] Int. Cl.$^6$ ........................................................ B65B 1/04
[52] U.S. Cl. .............................. 141/364; 141/18; 141/21; 141/292; 141/346; 141/369; 141/370; 141/373; 141/383; 141/386
[58] Field of Search ................................. 141/286, 86, 87, 141/18, 21, 291, 292, 364, 369, 370, 372, 373, 375, 379–381, 346, 383, 386; 128/200.14, 200.18, 200.19, 200.21, 203, 203.13, 203.14

[56] References Cited

U.S. PATENT DOCUMENTS

| | | | |
|---|---|---|---|
| 3,139,123 | 6/1964 | Lisciani | 141/286 |
| 3,565,133 | 2/1971 | Jones | 141/302 |
| 3,779,414 | 12/1973 | Jones . | |
| 5,293,913 | 3/1994 | Preszler | 141/364 |
| 5,505,236 | 4/1996 | Grabenkort et al. . | |

FOREIGN PATENT DOCUMENTS

WO 96/22804  8/1996  WIPO .

OTHER PUBLICATIONS

International Application No. PCT/US97/22462, International Search Report, dated Apr. 27, 1998.

*Primary Examiner*—J. Casimer Jacyna
*Assistant Examiner*—Timothy L. Maust
*Attorney, Agent, or Firm*—Neal D. Marcus

[57] ABSTRACT

A system is provided for draining an anesthetic agent from a reservoir of an anesthetic vaporizer. The system includes an anesthetic agent container having an inlet into which the agent can drain. The vaporizer has a draining station that defines an outlet and that defines a drain passage between the vaporizer reservoir and the outlet. A valve is operable to open and close the drain passage. A connector is provided with a receiving end for connecting to the draining station at the outlet. The connector has a discharge end for connecting to the container inlet. The connector holds the container below the draining station outlet and defines a transfer passage between the receiving end and the discharge end for draining the agent from the draining station into the container. Structural key configurations, uniquely associated with a specific anesthetic, are preferably provided at the connection of the container and connector and at the connection of the draining station and connector.

31 Claims, 9 Drawing Sheets

ANESTHETIC VAPORIZER DRAINING SYSTEM

CROSS-REFERENCE TO RELATED APPLICATION

Not Applicable

STATEMENT REGARDING FEDERALLY FUNDED SPONSORED RESEARCH OR DEVELOPMENT

Not Applicable

REFERENCE TO A MICROFICHE APPENDIX

Not Applicable

TECHNICAL FIELD

The present invention relates to a system for use in medical facilities to safely accommodate the draining of an unused quantity of a liquid anesthetic agent from a vaporizer after administration of the agent to a patient.

BACKGROUND OF THE INVENTION AND TECHNICAL PROBLEMS POSED BY THE PRIOR ART

Inhalable anesthetics (which are herein alternatively described as anesthetic agents) are typically volatile substances with relatively low boiling points and high vapor pressures. They can be flammable and explosive substances in both their liquid and vapor states. Further, inhalation of the vapor by health care personnel can cause drowsiness.

Therefore, such anesthetics must be safely handled in operating rooms in order to minimize the risk of inhalation by medical personnel as well as to minimize the risk of fire or explosion. Preferably, the anesthetic should be used in a way which will ensure that there is little or no release to the atmosphere at all stages of handling.

Anesthetics are typically dispensed in liquid form to an apparatus, such as an anesthetic vaporizer in an anesthesia machine. The vaporizer vaporizes the liquid anesthetic, and the anesthesia machine mixes the anesthetic vapor with oxygen and nitrous oxide. The mixture is supplied in gaseous form to the patient for inhalation.

Devices have been designed for the transfer of a liquid anesthetic from a supply container to a vaporizer through a closed system that minimizes the likelihood of the escape of an anesthetic liquid or gas to the atmosphere. The devices are designed so that during set-up and disassembly procedures, a supply container of anesthetic is not open and exposed to the atmosphere.

One system which has been developed for connecting an anesthetic container to a vaporizer is the QUIK-FIL™ vaporizer system sold by Abbott Laboratories, Inc., One Abbott Park Road, Abbott Park, Ill. 60064-3500, U.S.A.

The QUIK-FIL™ system includes a special filling inlet in an anesthetic vaporizer and includes a special mating anesthetic agent supply container having an opening through which the liquid anesthetic agent can be discharged. A valve member is provided in the container along with a first spring biasing the valve member to an extended, closed position occluding flow through the container opening. A container-receiving station or filling station on the anesthetic vaporizer defines the filling inlet and is adapted to matingly receive the container in an inverted orientation. The agent can be dispensed from the container into the filling inlet at the receiving station when the container valve member is automatically opened by proper engagement of the container by the receiving station structure.

In particular, a movable engaging member is provided on a valve inside the fill inlet in the receiving station along with a second spring for biasing the engaging member from a fully depressed, open position to an extended, closed position which seals the fill inlet closed. The engaging member is engagable with the container valve member and is urged to a fully depressed, open position when the container is inserted into the vaporizer receiving station. The second spring in the receiving station has less compression force than the first spring behind the container valve member so that the container valve member is moved away from the closed position by the engaging member in the filling inlet of the receiving station only after the engaging member has been first urged to the fully depressed, open position. The liquid agent can then flow from the container, past the open container valve member, through the vaporizer open valve, and into the vaporizer reservoir.

Some vaporizers are intended for use with only one specific anesthetic. In such situations, care must be taken to insure that only the proper anesthetic is dispensed into the particular vaporizer. To this end, the above-discussed QUIK-FIL™ filling system includes a keying system to prevent the use of the filling system with an anesthetic for which it is not designed.

In particular, the outlet end of the anesthetic container has projections of a specific shape, and the vaporizer fill inlet defines recesses having complementary shapes for mating with the container projections.

The above-described QUIK-FIL™ system is effective in transferring liquid anesthetic agent to the vaporizer. However, after the anesthetic has been administered to a patient or patients, some residual anesthetic may remain in the vaporizer. It is desirable to drain the residual anesthetic from the vaporizer. It is especially desirable to drain the vaporizer if the vaporizer is to be disconnected and removed from the anesthesia machine. If the anesthetic is drained from the vaporizer, then the vaporizer can be safely carried to another location for mounting to another anesthesia machine.

Heretofore, vaporizers have typically been emptied by opening a plug at the bottom of the vaporizer orifice and letting the anesthetic drain into an open receptacle or container held beneath the vaporizer. It would be desirable to provide an improved system for accommodating the draining of a vaporizer.

In particular, it would be desirable to provide a system for establishing a direct connection between the vaporizer drain and the receiving container. Further, it would be desirable to provide a system for assuring that the receiving container is securely maintained in a proper orientation without requiring that the container be held by an operator during the draining process.

It would also be advantageous to provide a draining system which could be readily used with an empty, or partly empty, container of the type used for filling the vaporizer. Preferably, the draining system should also accommodate containers of the self-closing type, and components of the draining system should preferably be readily connectable to such a container and should operate to readily open such a container upon establishing a proper connection.

It would also be desirable to provide a draining system which would be effective to prevent a vaporizer designated for use with one particular type or brand of anesthetic from being connected so as to drain into a container intended for another type of anesthetic. To this end, it would be advantageous to provide a draining system which would function only with the specific type of container that must be used to fill the vaporizer.

The draining system should also desirably function to minimize anesthetic waste through evaporation or anesthetic spillage, and minimize retention of residual transfer volumes of the anesthetic. Further, the draining system should preferably be very user friendly and should not interfere with the anesthesia machine operation.

When a vaporizer is disconnected and removed from an anesthesia machine, the vaporizer may be temporarily placed on a counter or table prior to, or after, transporting the vaporizer to another location. The vaporizer is typically disposed on its base in an upright orientation on such a counter or table—especially if there is residual anesthetic in the vaporizer. To accommodate this, it would be advantageous to provide a draining system that does not have stationary features projecting from, or below, the vaporizer base which would interfere with resting the vaporizer on its base.

Finally, it would be beneficial if the draining system could accommodate designs of components that are relatively inexpensive to manufacture.

The present invention provides an improved anesthetic draining system which can accommodate designs having the above discussed benefits and features.

SUMMARY OF THE INVENTION

One aspect of the invention includes a draining system for draining a liquid anesthetic agent from a reservoir of an anesthetic vaporizer. The system includes an anesthetic agent container defining an inlet into which the agent can drain. The system also includes a draining station on the vaporizer. The draining station has an outlet and defines a drain passage communicating between the vaporizer reservoir on one end and the outlet on the other end. The draining station includes a valve operable to open and close the drain passage.

A connector is provided with a receiving end for contacting to the draining station at the outlet. The connector has a discharge end for connecting to the container inlet. The connector is configured to support the container below the draining station outlet. The connector defines a transfer passage between the receiving end and the discharge end for draining the anesthetic agent from the draining station on the vaporizer into the container.

According to another aspect of the invention, a separate connector per se is provided for connecting a container to a draining station on an anesthetic vaporizer which has a reservoir of liquid anesthetic agent and wherein the draining station has (A) a drain passage communicating between the reservoir on one end and an outlet on the other end, and (B) a valve operable to open and close the drain passage. The container defines an inlet into which the agent can drain. The connector includes a structure having a receiving end for connecting to the draining station at the outlet. The connector structure also has a discharge end for connecting to the container inlet. The connector structure has a configuration for supporting the container below the draining station outlet. The connector structure defines a transfer passage between the receiving end and the discharge end for draining the agent from the draining station into the container.

In a preferred embodiment, the connector structure includes two relatively movable components. The first component includes a funnel or collecting receptacle at the receiving end. Preferably, two flanges extend in opposite directions from the top of the collecting receptacle at the receiving end for being received in complementary slots in the draining station on the vaporizer. One of the flanges can be made thicker than the other of the flanges, and one of the slots on the draining station can be made thicker so that a connector with only the particular flanged configuration can be connected to the draining station. In that way, a key system can be provided for a specific kind of anesthetic which is intended to be used only in that type of vaporizer.

The connector first component also preferably includes a rigid conduit member extending from the collecting receptacle. The rigid conduit member defines a transfer passage communicating with the collecting receptacle. The rigid conduit member has a distal end at the connector discharge end. The conduit member has an external male thread adjacent the distal end for threadingly engaging a female thread in the neck of the container into which the residual anesthetic liquid is to be drained.

The rigid conduit member of the connector first component preferably further has (1) a longitudinal support wall extending across a longitudinal cross-section of the transfer passage and extending adjacent the distal end of the conduit member. The conduit member also further has an engaging boss which projects from the support wall for engaging a valve member in the container into which the anesthetic liquid is to be drained. The boss has a size and shape that permits the liquid to flow out of the transfer passage and around a boss into the container.

A connector second component is preferably a generally annular sleeve which is rotatable on the rigid conduit member. Preferably, the sleeve includes an inwardly extending flange on one end for being received in an external, circumferential groove defined by the rigid conduit member. This permits the sleeve to be retained on the rigid conduit member while accommodating relative rotation between the conduit member and sleeve.

In the preferred form, the sleeve has an interior wall surface which is generally cylindrical. A plurality of recesses are defined by the sleeve in the interior wall surface and these recesses are open at the end of the sleeve. The recesses are adapted to receive complementary protuberances on the neck of the container into which the liquid anesthetic is to be drained. This functions as a key system which prevents attachment of a container to a connector wherein the container and connector do not have complementary protuberances and recesses, respectively. Thus, the container and sleeve of the connector can be designated for use with only a particular type of anesthetic. This can be accomplished by supplying to healthcare professionals a particular anesthetic only in a container having a predetermined key system defined by the protuberances on the container neck or defined by other suitable key structures complementary with mating structures on the sleeve of the connector.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same, FIG. 1 shows the vaporizer and related draining system components prior to assembly of the components;

DESCRIPTION OF THE PREFERRED EMBODIMENT

Figure 1:
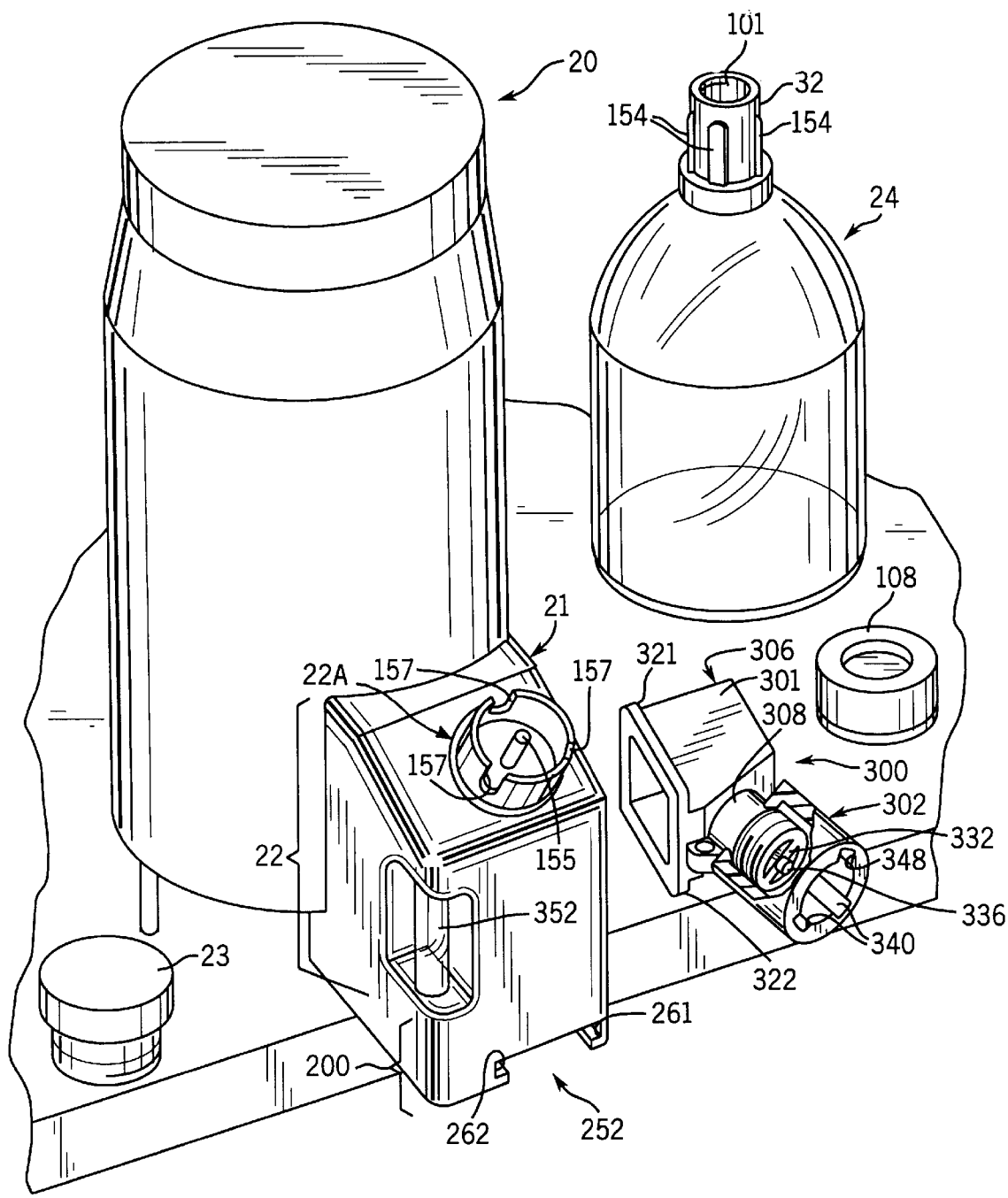
FIG. 1 is a perspective view of the draining system for draining a liquid anesthetic agent from an anesthetic vaporizer into a container in accordance with the principles of the present invention, and more particularly.

The present invention provides a novel system which includes apparatus for connecting an anesthetic container to a vaporizer for draining the vaporizer. The system can be provided in a number of different designs incorporating a variety of different features and capabilities.

The system accommodates the safe handling of liquid anesthetic agents in operating rooms in order to minimize the risk of inhalation by medical personnel as well as to minimize the risk of fire or explosion.

The system permits residual anesthetic to be easily drained from a vaporizer into a storage container. In a preferred form of the invention, the draining system allows the residual anesthetic to be drained into an empty, or partly empty, container of the same type used for filling the vaporizer. In this preferred form of the invention, the system functions to prevent the draining of the vaporizer designated for one particular type or brand of anesthetic from being drained into a container designed for another type of anesthetic.

In the preferred form of the invention, the draining system securely holds and supports the container in a proper orientation below the vaporizer without requiring that the container be held by an operator. When not in use to drain anesthetic from the vaporizer, the system has no components projecting below the bottom of the vaporizer that would hinder removal of the vaporizer from an anesthetic machine and that would prevent the temporary placement of the removed vaporizer on its base on a table, counter, or the like.

The draining system of the present invention minimizes anesthetic waste through evaporation and anesthetic spillage, and minimizes retention of residual transfer volumes of the anesthetic. The draining system is user friendly and does not interfere with the anesthesia machine operation.

The draining system accommodates design of components which are relatively inexpensive to manufacture and which are easy to handle and use.

While this invention is susceptible of embodiment in many different forms, this specification and the accompanying drawings disclose only one specific form as an example of the invention. The invention is not intended to be limited to the embodiment so described, however. The scope of the invention is pointed out in the appended claims.

For ease of description, the system components of this invention are described in the normal storage and operating positions, and terms such as upper, lower, horizontal, etc., are used with reference to these positions. It will be understood, however, that the components of this invention may be manufactured, stored, transported, and sold in an orientation other than the positions described.

Figures illustrating the components of the invention and related equipment show some mechanical elements that are known and that will be recognized by one skilled in the art. The detailed descriptions of such elements are not necessary to an understanding of the invention and, accordingly, are herein presented only to the degree necessary to facilitate an understanding of the novel features of the present invention.

Figure 4:
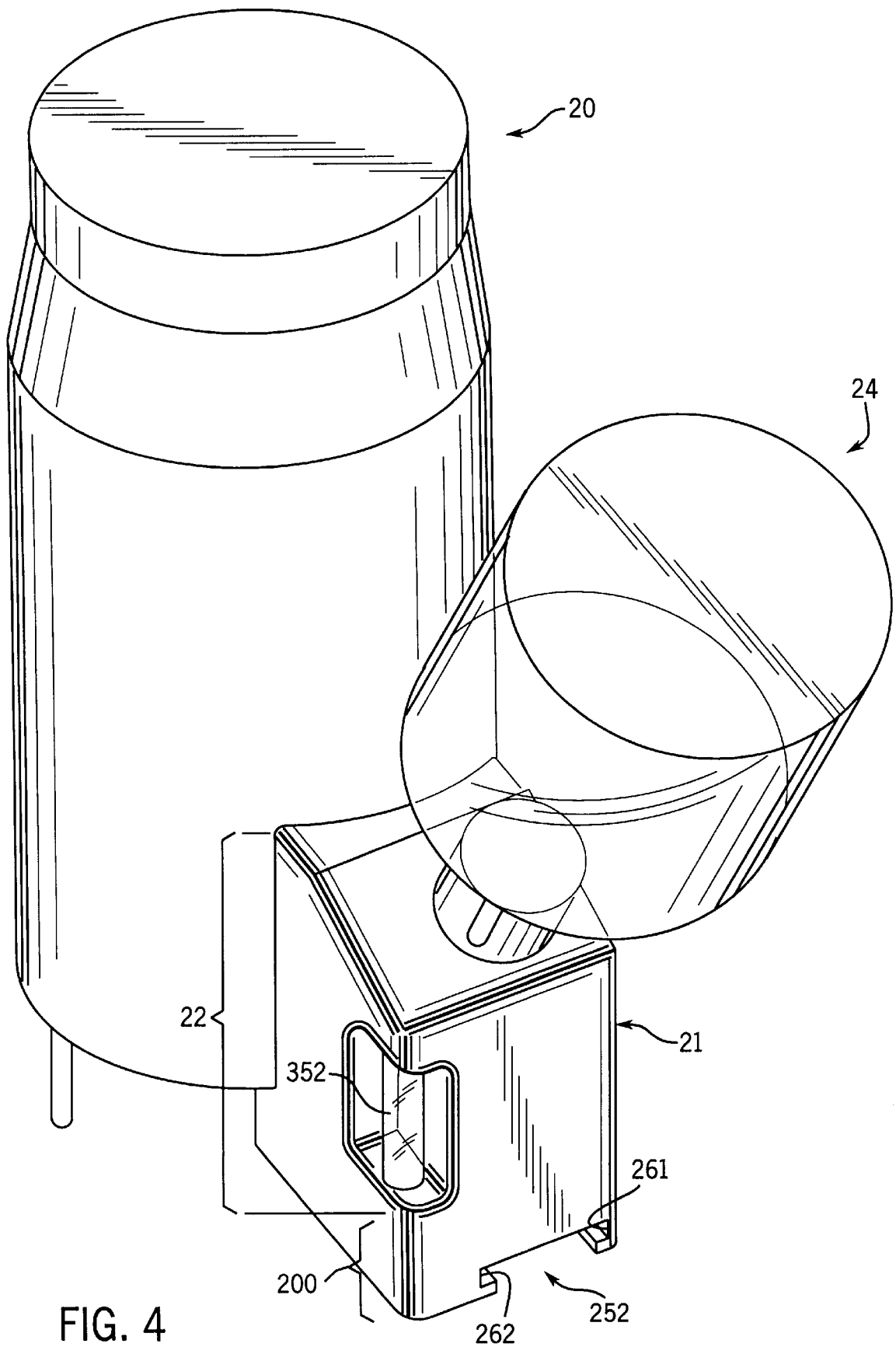
FIG. 4 is a perspective view of the anesthetic agent container inverted and mounted in a receiving station or filling station above the draining station in a fill and drain block on an anesthetic vaporizer.

With reference to FIG. 1, reference number 20 generally designates a vaporizer which is adapted to be mounted to an anesthesia machine (not illustrated). The vaporizer 20 can be filled with a liquid anesthetic agent and can then be subsequently drained after use. To this end, the vaporizer 20 is provided with a fill and drain block 21. The upper portion of the block 21 includes a receiving or filling station 22 for receiving an inverted, anesthetic agent, supply container or storage container 24 as shown in FIG. 4. The filling station 22 has a fill inlet 22A normally covered with a removable cap 23. Except for the fill and drain block 22, the structure and operation of the vaporizer 20 may be in accordance with any conventional or special design, the details of which form no part of the present invention.

In one preferred embodiment of the present invention, the container 24 may be the same container as employed in the above-described QUIK-FIL™ system sold by Abbott Laboratories, Inc. A substantially similar container 224 is described in the U.S. Pat. No. 5,505,236 with reference to FIGS. 13–14 of that patent.

Figure 2:
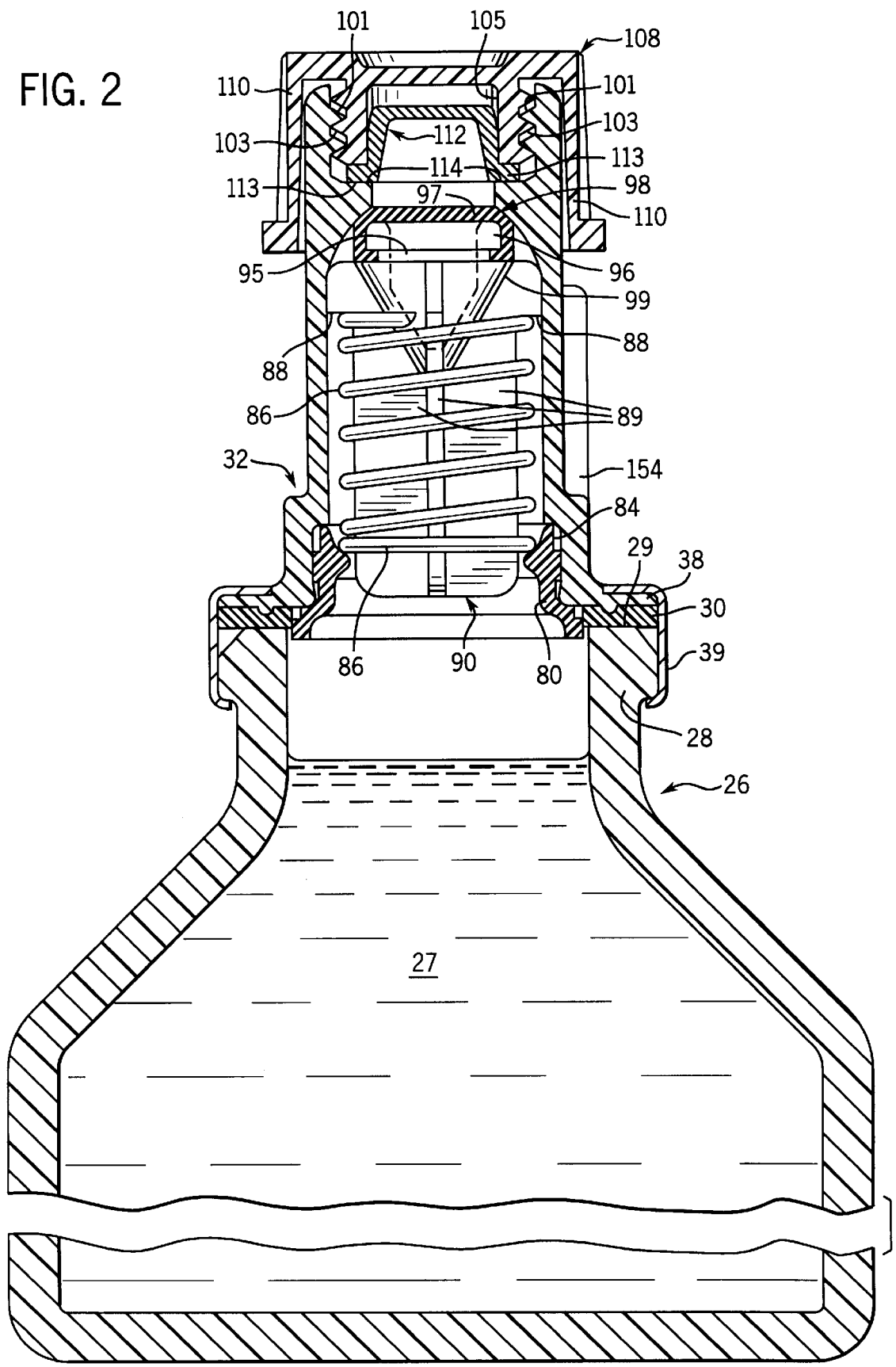
FIG. 2 is a fragmentary, cross-sectional view of a preferred embodiment of a container from which a liquid anesthetic agent can be dispensed and into which residual liquid anesthetic agent can be drained, and the container is shown in a closed condition with an overcap installed thereon.
Figure 3:
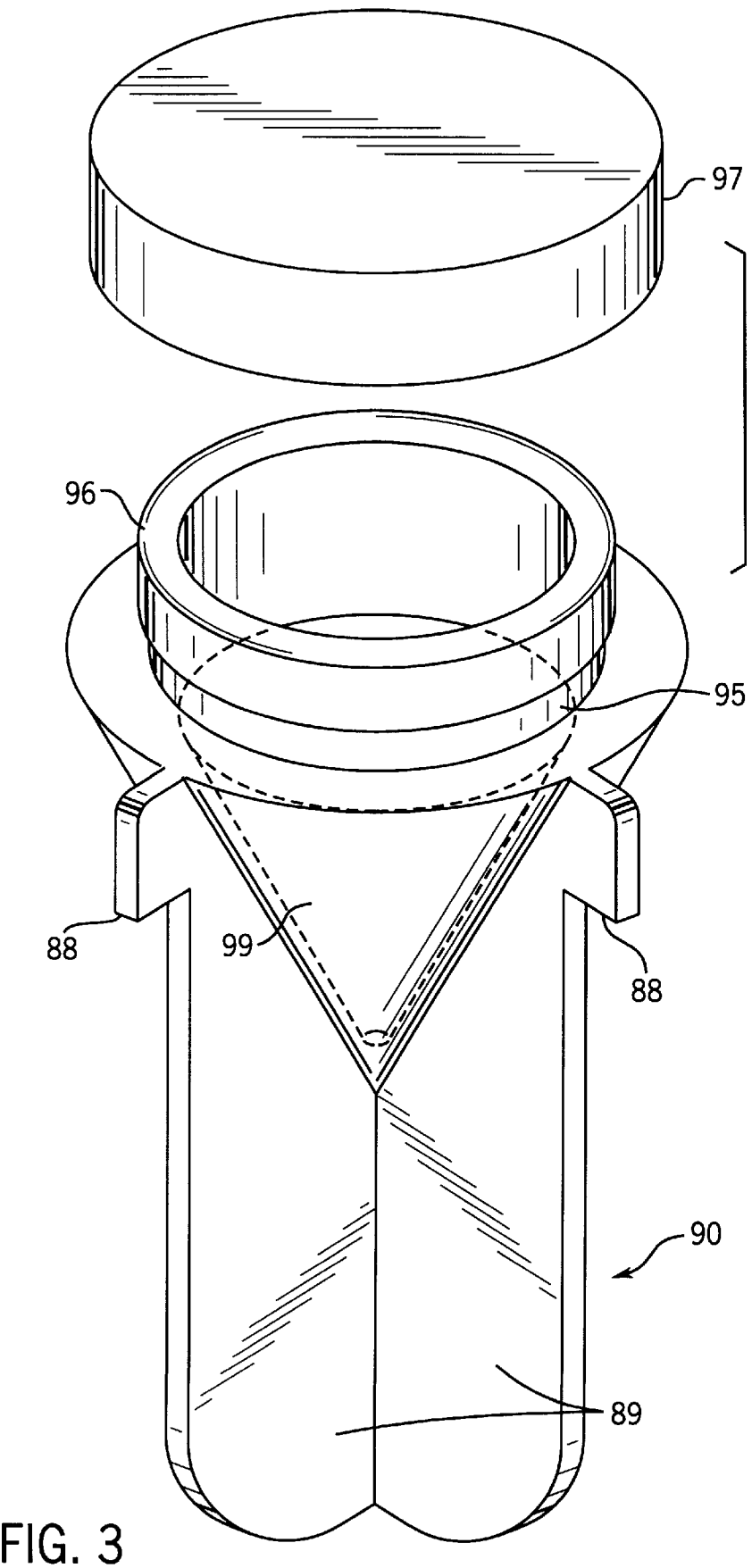
FIG. 3 is a perspective view of the plunger or valve member of the container shown in FIG. 2.

As shown herein in FIGS. 2 and 3, the container 24 includes a body or body portion 26. The body portion 26 contains the liquid anesthetic agent 27. When the container 24 is inverted and an internal valve is automatically opened in the filling station 22 (in a manner described in detail in U.S. Pat. No. 5,505,236), the liquid agent 27 flows by gravity into the filling station to fill the reservoir 210 (FIG. 5) within the vaporizer 20.

The container body 26 (FIG. 2) terminates in an upper flange 28 defining an annular end surface 29. Mounted to the top of the flange 28 is a gasket 30 which is preferably low density polyethylene.

The container 24 includes a spout or neck 32 (FIG. 2) which can function as an outlet and as an inlet. The neck 32 has a base flange 38 disposed on the gasket 30. An aluminum ferrule 39 is crimped around the components to hold them in place. The interior of the neck 32 communicates with the liquid agent 27 in the body 26.

A spring retainer 80 is press fit into an annular channel 84 at the bottom of the inside cylindrical wall of the neck 32. The retainer 80 supports the bottom of a compression spring 86 which has a top end biased against outwardly extending portions 88 of four crosswalls 89 which define an internal plunger 90 (FIG. 3).

The top of the plunger 90 includes a valve member or head 96 (FIG. 3) surrounded by a reduced diameter neck or groove 95 for snap-fit engagement of a sealing cap 97. The sealing cap 97 is preferably fabricated from low density polyethylene and is adapted to engage, and tightly seal against, an arcuate, concave valve seat 98 defined by the inside surface of the container neck 32. The upper, peripheral edge of the sealing cap 97 defines a sealing surface for engaging the valve seat.

Preferably, the plunger 90 has a conical formation 99 extending from the tops of the walls 89 and converging inwardly of the sealing cap 97.

The interior, upper end of the neck 32 defines a thread 101 for threadingly engaging a thread 103 on an inwardly projecting, inner skirt 105 of an overcap 108. The overcap 108 includes a downwardly projecting, outer skirt 110. A low density polyethylene cap gasket 112 is disposed within the inner skirt 105 and has a peripheral flange 113 which is sealingly compressible between the bottom of the inner skirt 105 and an annular shoulder 114 in the container neck 32 below the neck thread 101 to engage the annular end surface of the container neck 32.

The exterior of the container neck 32 preferably includes three, equally spaced keys or ribs 154 (FIGS. 1 and 2) for aligning with, and being received within, three mating grooves or recesses 155 (FIG. 1) in the inlet filling station of the drain block 22. This permits a specific type of vaporizer to be used only with a specific type of container having the appropriate rib configuration.

The size, shape, and spatial orientation of the ribs may be established for a particular anesthetic agent supplied in the container 24. Other anesthetic agents would be provided in containers having a different rib arrangement for use with vaporizers having appropriate complementary or mating recesses. The rib arrangement is thus agent-specific, and will permit the insertion of a specific agent container in only a specific vaporizer designed for that container and anesthetic agent. Other shapes of complementary protuberances and complementary recesses could be provided as engaging key structures if desired.

In order to fill the vaporizer 20, the vaporizer inlet cap 23 is first removed. Then the overcap 108 is removed from the container 24, and the container 24 is inverted to dispose the container neck 32 within the fill inlet 22A of the vaporizer inlet fill station 22 in the fill and drain block 21 as shown in FIG. 4.

Figure 5:
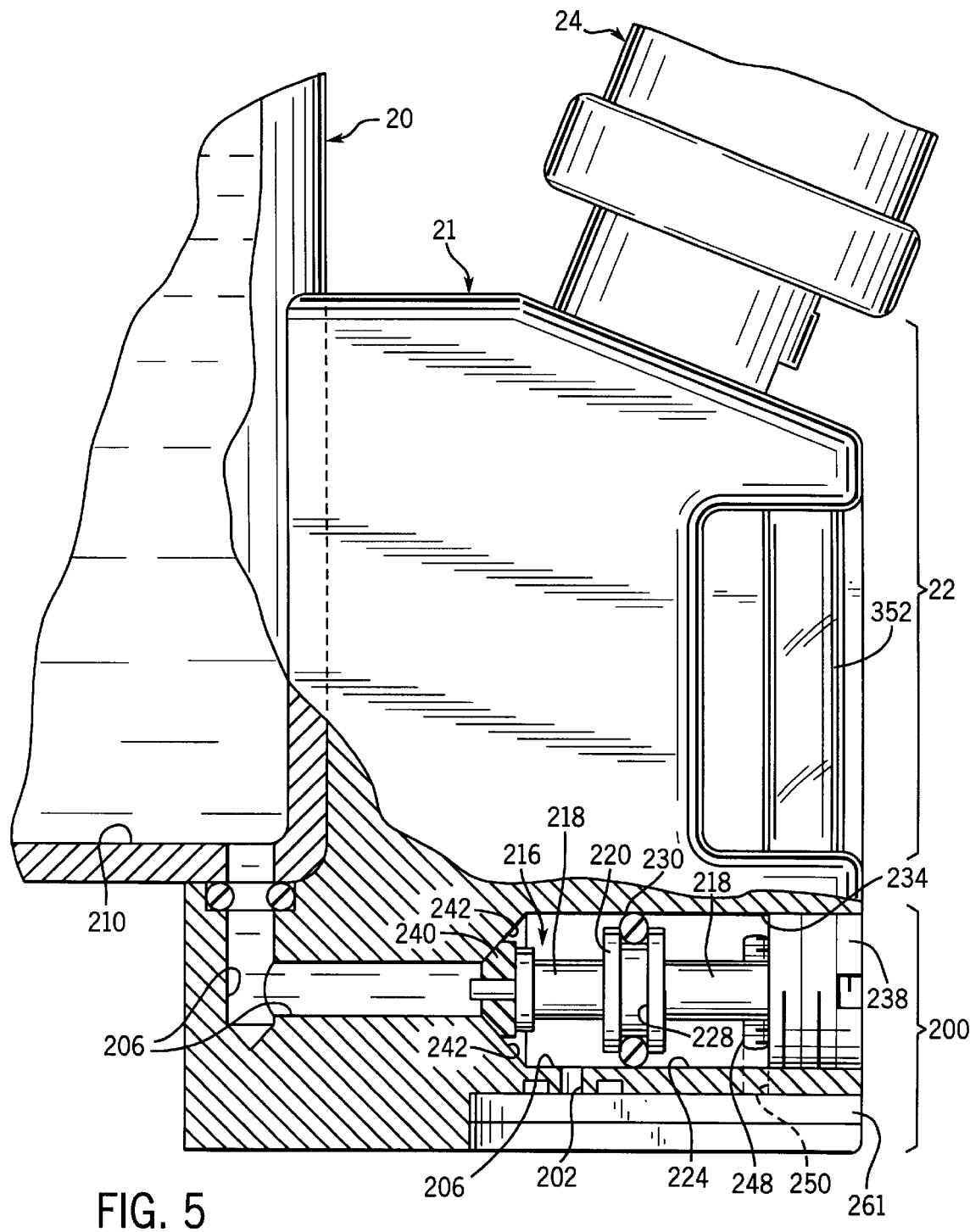
FIG. 5 is a fragmentary, cross-sectional view of the components shown in FIG. 4.

When the inverted container 24 is mounted in the fill inlet 22A of the fill and drain block 21, the container valve member 96 is automatically opened by an engaging member 157 (FIG. 1) in the fill inlet 22A of the block 21 so that the liquid anesthetic agent can flow by gravity into the vaporizer reservoir 210 (FIG. 5). The vaporizer filling operation is described in detail in the U.S. Pat. No. 5,505,236 with reference to the substantially similar container 224 illustrated in FIGS. 13–14 of that patent. The disclosures of the U.S. Pat. No. 5,505,236 are incorporated herein by reference thereto to the extent pertinent and to the extent not inconsistent herewith.

The structure of the fill inlet 22A in the fill and drain block 21, the process by which the container 24 is mounted in the fill inlet 22A, and the manner in which the container valve member 96 is opened by the engaging member 157 within the fill inlet 22A form no part of the present invention.

After the vaporizer 20 and anesthesia machine in which the vaporizer is mounted have been used to administer the anesthetic to a patient, the residual liquid anesthetic remaining in the vaporizer reservoir 210 (FIG. 5) may be drained from the vaporizer using the system of the present invention. To this end, the lower portion of the fill and drain block 21 includes a draining station 200 (FIGS. 1 and 5).

The draining station 200 has an outlet 202 and defines a drain passage 206 communicating between the vaporizer reservoir 210 on one end and the outlet 202 on the other end. The draining station 200 includes a valve 216 operable to open and close the drain passage 206.

In particular, the valve 216 includes a shaft 218 and a larger diameter cylindrical portion 220 extending into a generally cylindrical side passage or bore 224 communicating with the drain passage 206. The enlarged cylindrical portion 220 defines a groove 228 in which is disposed an O-ring 230 which sealingly engages the interior cylindrical surface of the side passage or bore 224.

The bore 224 includes an internally threaded end portion 234 which opens at the exterior side of the fill and drain block 21. The outer end of the valve 216 includes a screw head adjustment portion 238 which is threadingly engaged with the internally threaded portion 234 of the bore 224.

The innermost end of the valve 216 includes a valve member 240. The valve member 240 preferably has a hemispherical or parabolic configuration and may include a soft seal material, such as a soft, thermoplastic material. The valve member 240 is adapted to seat and seal against a frustoconical shoulder 242 defined between two different diameters of the drain passage 206.

Rotation of the screw head portion 238 of the valve 216 in one direction causes the valve member 240 to be moved inwardly against the valve seat 242 in sealing engagement so as to occlude or close the drain passage 206. Rotation of the screw head adjustment portion 238 in the opposite direction causes the valve member 240 to move outwardly away from the valve seat 242 so as to open the drain passage 206.

Figure 6:
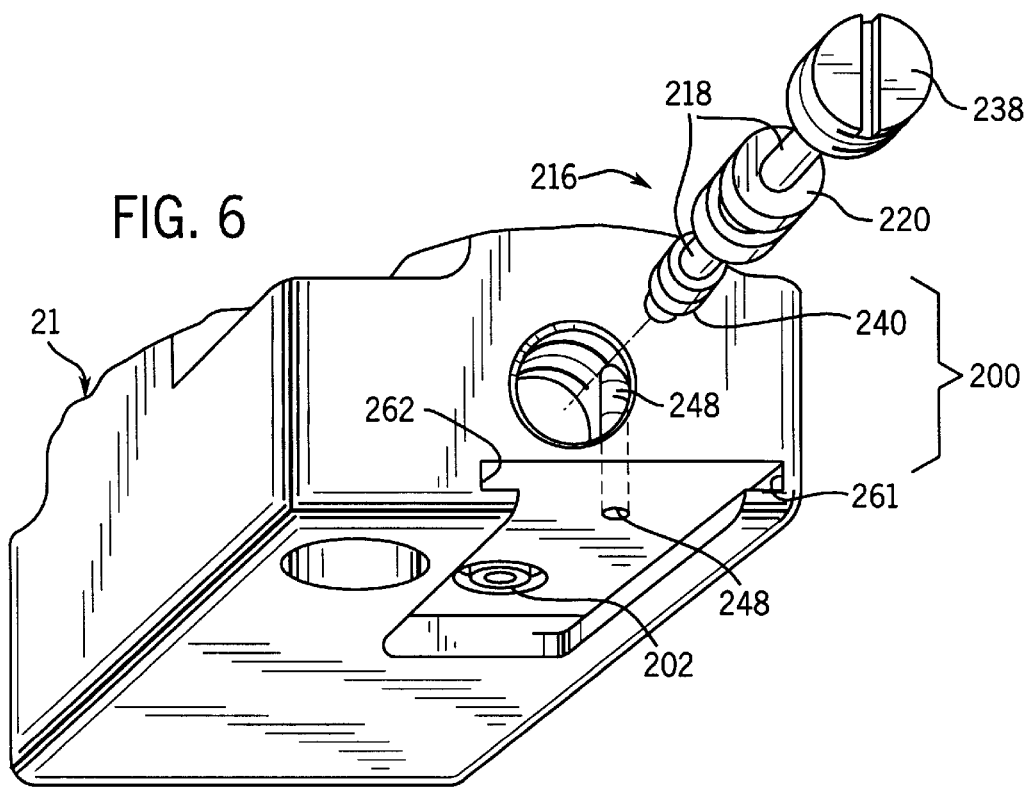
FIG. 6 is an exploded, bottom, perspective view of the draining station portion of the fill and drain block shows in FIGS. 4 and 5.

A set screw retention pin 248 (FIGS. 5 and 6) is disposed in a threaded bore 250 within the draining station 200. The pin 248 extends into the valve bore 224 adjacent the valve shaft 218 and between the valve screw head adjustment portion 238 and the valve enlarged cylindrical portion 220. The pin 248 thus prevents the valve 216 from being inadvertently removed entirely from the fill and drain block 21 unless the set screw pin 248 is first removed from the fill and drain block 21.

As shown in FIG. 1, the draining station 200 of the fill and drain block 21 has a recess 252 which opens downwardly at the bottom of the block 21 and which defines a first slot 261 and a second slot 262. The thickness of the slot 261 is less than the thickness of the slot 262. The slots define mating structural key configurations for receiving a connector 300 (FIGS. 1 and 7).

Figure 7:
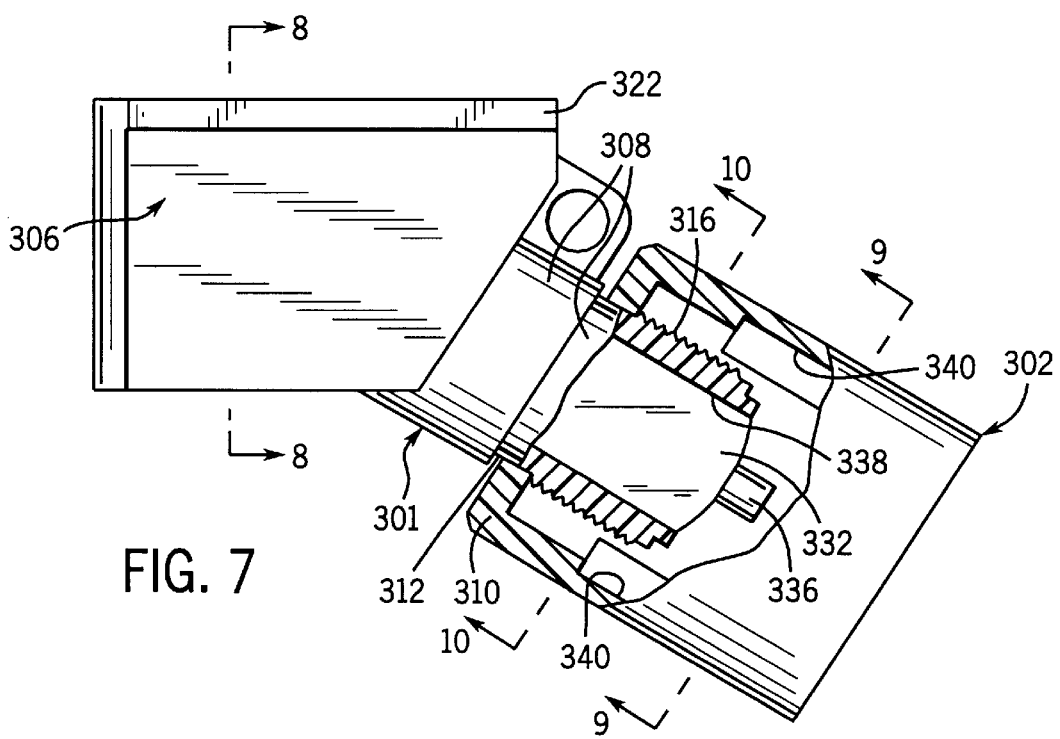
FIG. 7 is a side elevational view, with portions broken away to show interior details in partial cross section, of the draining system connector of the present invention.

The connector 300, in the preferred form, is a two-component structure that includes a first rigid component 301 and a second rigid component 302 (FIG. 7). The first rigid component 301 includes a receiving end defined by a collecting receptacle or funnel 306. The first component 301 also includes an extending conduit member 308 on which the second component 302 is rotatably mounted.

In the preferred embodiment, the second component 302 is a generally cylindrical sleeve having an annular shoulder 310 (FIG. 7) on one end. The annular shoulder 310 is received within an annular groove 312 defined by the conduit member 308.

The conduit member 308 also includes an enlarged, exterior threaded portion 316. The portion 316 has a diameter which is greater than the inner diameter of the annular shoulder 310 of the second component sleeve 302. This prevents the sleeve 302 from being removed from the conduit member 308.

Figure 8:
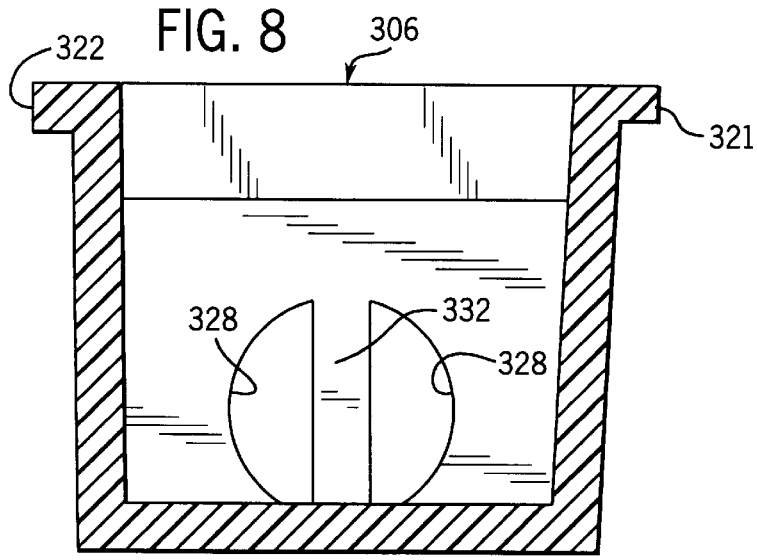
FIG. 8 is a cross-sectional view taken generally along the plane 8—8 in FIG. 7.
Figure 13:
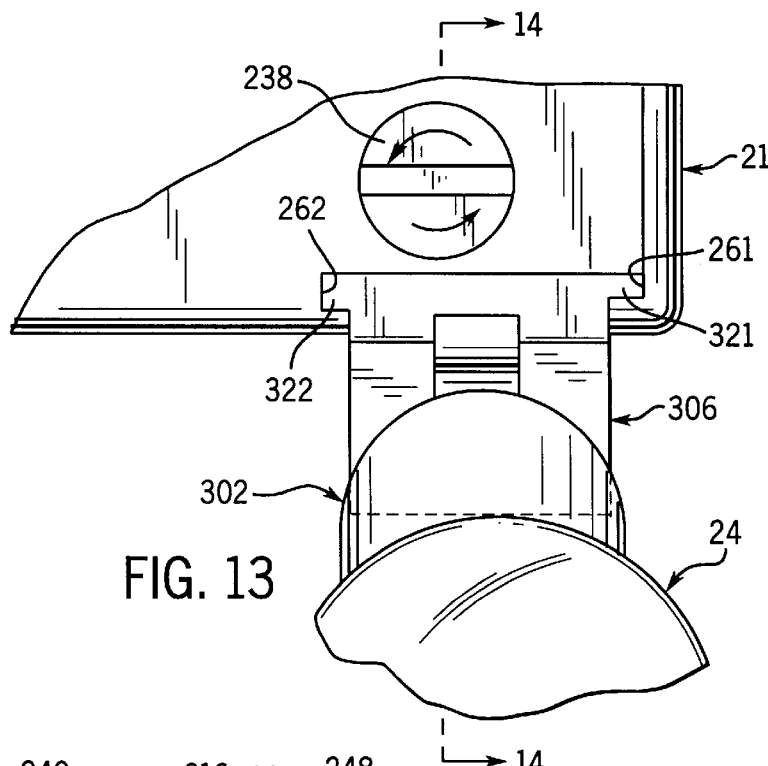
FIG. 13 is a fragmentary, front elevational view showing the connector, with the container attached, inserted into the outlet of the draining station portion of the fill and drain block on the vaporizer.
Figure 14:
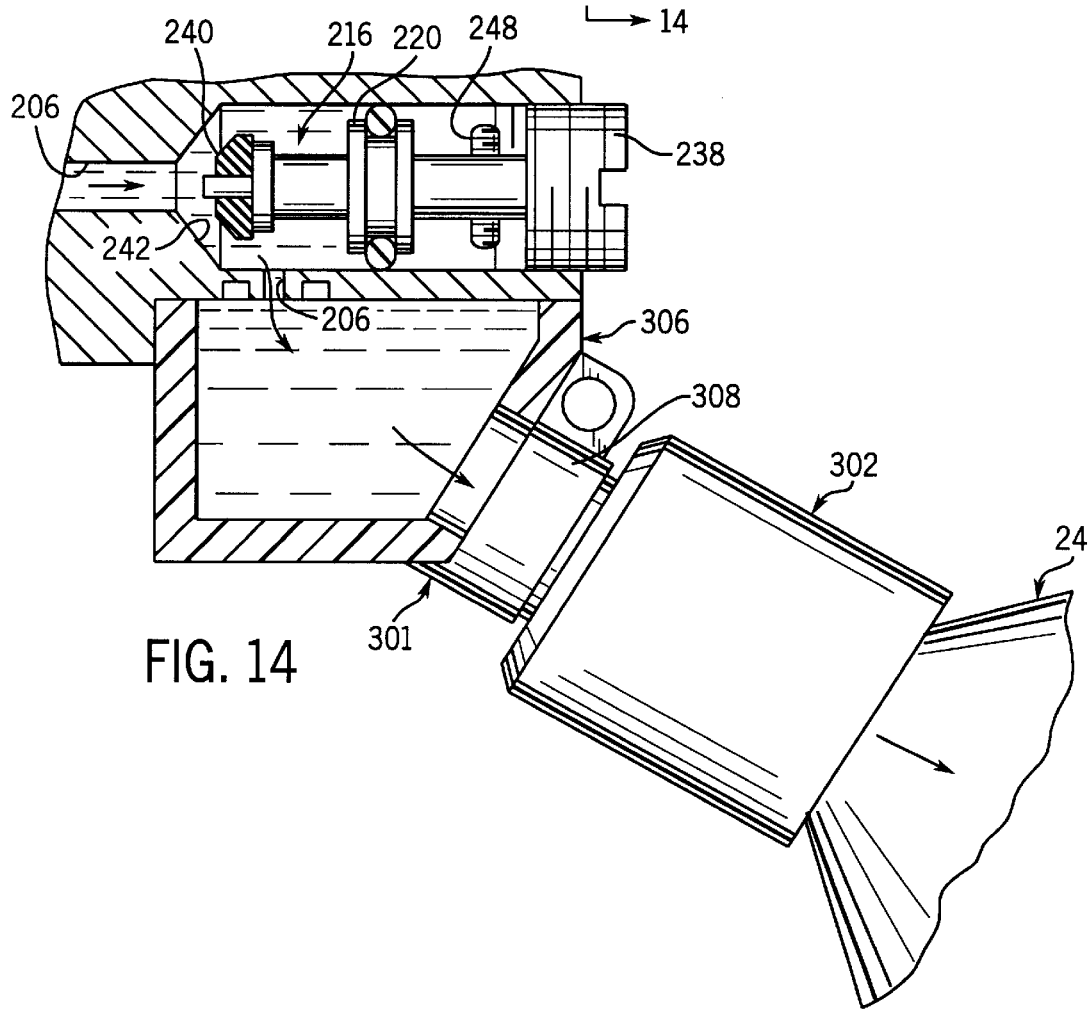
FIG. 14 is a side-elevational view of the assembly shown in FIG. 12 with portions broken away to illustrate interior details and with some of the components shown in cross section.

As shown in FIGS. 1, 8, and 13 the funnel 306 includes a first flange 321 and a second flange 322. The first flange 321 is thinner than the second flange 322 and is adapted to be slidingly received in the first slot 261 of the draining station 200 on the fill and drain block 21. The funnel flange 322 is adapted to be slidingly received in the second slot 262 of the fill and drain block 21. The funnel 306 can thus be positioned under the outlet 202 of the draining station 200 in the fill and drain block 21.

Figure 9:
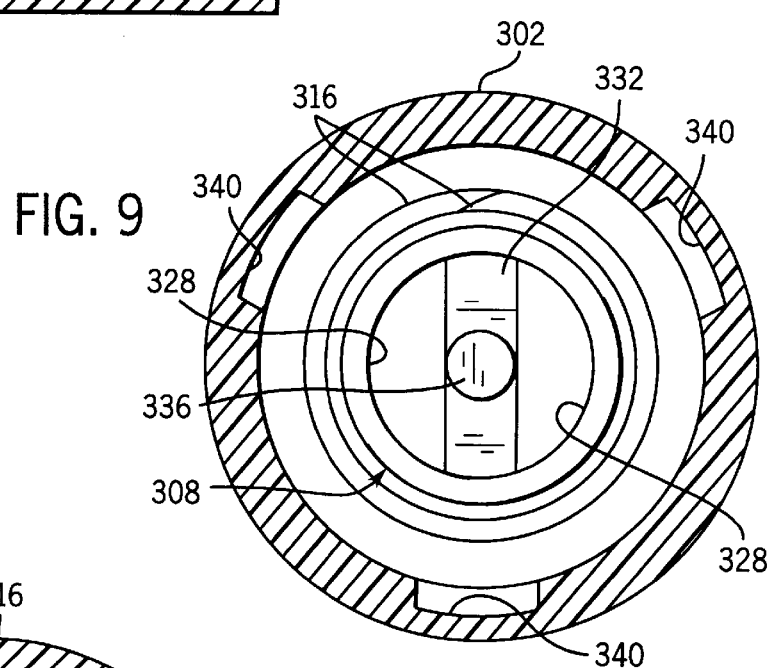
FIG. 9 is a cross-sectional view taken generally along the plane 9—9 in FIG. 7.
Figure 10:
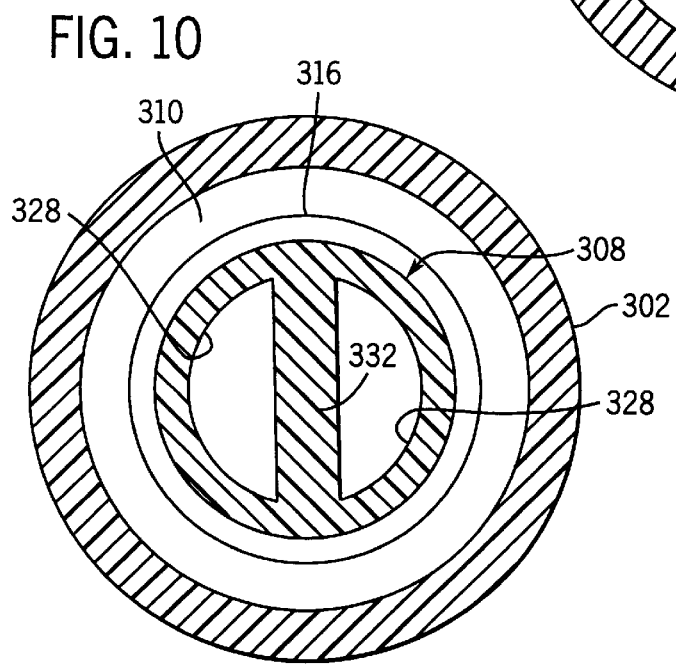
FIG. 10 is a cross-sectional view taken generally along the plane 10—10 in FIG. 7.

As shown in FIG. 8, a lower portion of one end wall of the funnel 306 communicates with a transfer passage 328 defined through the interior of the conduit member 308 (FIGS. 7, 9, and 10).

The transfer passage 328 in the conduit member 308 contains a longitudinally extending support wall 332 which extends along the longitudinal cross section of the transfer passage 328 to divide it into two, equal passage portions. The wall 332 extends to the distal end of the conduit member 308 and supports a reduced-diameter engaging boss 336 which has a generally cylindrical configuration. Liquid flowing through the transfer passage 328 from the receptacle or funnel 306 can discharge from the transfer passage 328 around the reduced-diameter engaging boss 336. The engaging boss 336 is designed to engage the container valve member cap 97 (FIG. 2) as described in detail hereinafter.

As can be seen in FIGS. 1 and 10, the second component sleeve 302 defines three, equally spaced, longitudinally oriented, recesses or channels 340. The channels or recesses 340 are adapted to receive the container neck ribs 154 as described in more detail hereinafter.

Figure 11:
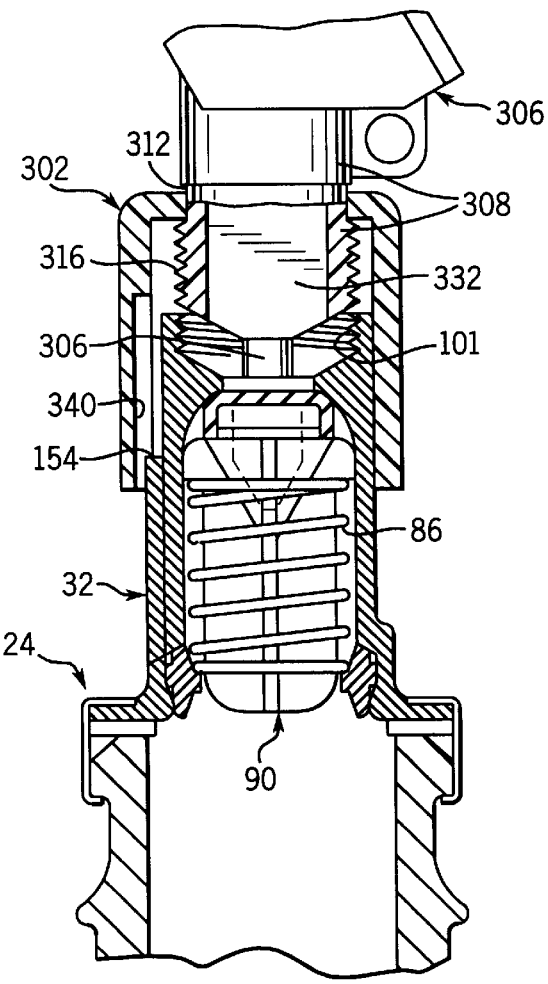
FIG. 11 is a fragmentary, cross-sectional view showing the connector partially inserted into the container.

The draining system components may be employed to drain residual liquid anesthetic agent from the vaporizer 20. This may be conveniently effected by first attaching the connector 300 to an empty or partly empty container 24. To this end, the container cap 108 is unscrewed from the container neck 32 (FIG. 2). Then the connector 300 is attached to the container neck 32. This is accomplished by effecting relative axial movement between the connector sleeve 302 and the container neck 32. The sleeve 302 may have to be rotated to align the recesses 340 with the container neck ribs 154 as shown in FIG. 11.

Figure 12:
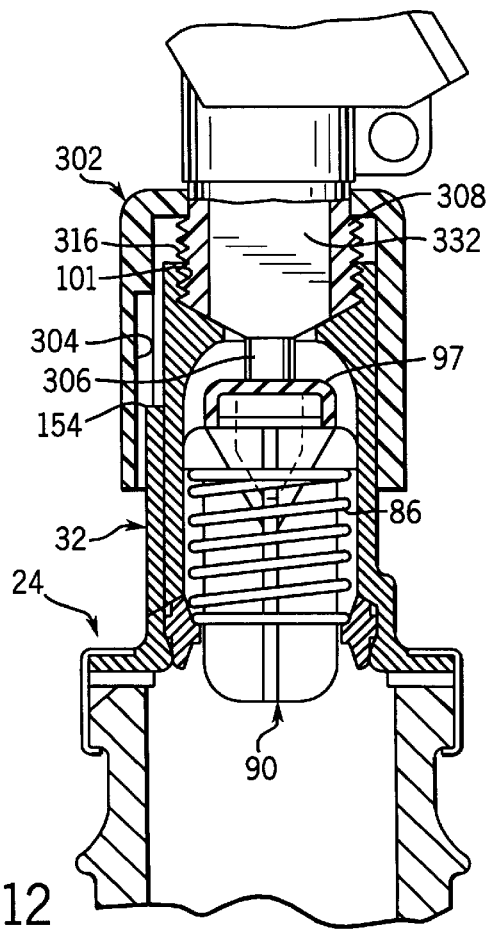
FIG. 12 is a view similar to FIG. 11, but FIG. 12 shows the connector fully inserted into the container.

Initially, the container valve member 96 (and sealing cap 97 carried thereon) remain closed as shown in FIG. 10. After the connector sleeve 302 has been moved axially onto the container neck 32 a sufficient distance, the threads 316 on the connector conduit member 308 are axially located to begin threadingly engaging the container neck internal threads 101. The connector first component 301 (which includes the conduit member 308 and attached collecting receptacle 306) can then be rotated to effect rotation of the threads 316 and establish a threaded engagement with the threads 101 on the container neck 32 as shown in FIG. 12. This pulls the connector 300 further into the container neck 32 so that the engaging boss 336 engages the container valve sealing cap 97 to urge the sealing cap (97), and entire associated plunger 90, away from the container valve seat 98 as shown in FIG. 12. This opens the container 24.

The connector 300, with the open container 24 attached, is then connected to the fill and drain block 21 by sliding the funnel flanges 321 and 322 into the fill and drain block slots 261 and 262, respectively. When the funnel 306 is properly disposed within the recess below the outlet 202 of the draining station 200, the connector 300 maintains the open container 24 in an upwardly angled, receiving orientation below the elevation of the drain outlet 202. The draining system valve 216 can be turned by its adjustment portion 238 to open the valve so that the residual liquid anesthetic agent in the vaporizer reservoir 210 (FIG. 5) can drain through the drain passage 206, through the outlet 202, into the funnel 306, through the connector transfer passage 328, and into the container 24.

The operator does not need to manually support the container 24. The connected drain system components permit the liquid anesthetic to drain into the container 24 through the connector 300 so that the potential for loss of anesthetic through spillage or evaporation is minimized. Further, the novel connector 300 has no internal features that would retain any significant amount of the liquid anesthetic.

When all of the residual liquid anesthetic agent has drained from the vaporizer reservoir (as may be determined from a conventional site glass 352 (FIGS. 1, 4, and 5) on the reservoir, or by other suitable means), the connector 300 and container 24 may be removed. To this end, the valve 216 in the draining station is closed, and then the connector 300 and attached container 24 are pulled outwardly so that the funnel 306 slides out from beneath the fill and drain block 21.

The container 24 is then oriented generally vertically with the base down so that the connector 300 can be unscrewed (whereby the sleeve 302 can be slid off of the container neck). As the connector 300 is unscrewed from the container 24, the container valve sealing cap 97 on the plunger 90 is urged by the container spring 86 to close and seal against the valve seat 98 in the container 24. The overcap can then be screwed back onto the container 24.

It will be appreciated that because the funnel flanges 321 and 322 and the mating slots 261 and 262 in the draining station 200 define a key system, only an appropriately designed connector 300 intended for use with the particular vaporizer 20 and anesthetic will be properly connectable to the vaporizer draining station 200. Similarly, because the recesses 340 of the connector sleeve 302 are shaped to matingly engage only the particular configuration of the ribs 154 on the neck of the container 24, the connector 300 can be attached only to the particular container 24 with which it is intended to be used and which is designed to hold only a particular type of anesthetic.

It will be readily apparent from the foregoing detailed description of the invention and from the illustrations thereof that numerous variations and modifications may be effected without departing from the true spirit and scope of the novel concepts or principles of this invention.

What is claimed is:

1. A draining system for draining a liquid anesthetic agent from a reservoir of an anesthetic vaporizer, said system comprising:

(A) an anesthetic agent container defining an inlet into which said agent can drain;

(B) a draining station on said vaporizer, said draining station having an outlet and defining a drain passage communicating between said vaporizer reservoir on one end and said outlet on the other end, said draining station including a valve operable to open and close said drain passage; and (C) a connector having a receiving end for connecting to said draining station at said outlet and having a discharge end for connecting to said container inlet, said connector configured to support said container below said draining station outlet so as to preclude any movement of the container with respect to the connector and defining a transfer passage between said receiving end and said discharge end for draining said agent from said draining station into said container.

2. The system in accordance with claim 1 in which said draining station and connector define first mating structural key configurations.

3. The system in accordance with claim 2 in which said connector defines first and second flanges at said receiving end, said flanges having different thicknesses;

said draining station defines first and second slots of differing thicknesses for matingly receiving said first and second flanges, respectively; and said first mating structural key configurations are defined by said slots and flanges.

4. The system in accordance with claim 3 in which said connector includes a collecting receptacle that (1) is disposed between, and connected to, said flanges, (2) defines between said flanges an opening that can be positioned at said draining station outlet adjacent said drain passage, and (3) communicates with said connector transfer passage.

5. The system in accordance with claim 1 in which said connector and container define second mating structural key configurations.

6. The system in accordance with claim 5 in which said second mating structural key configurations include one of said container and connector having at least one projection, and the other of said container and connector having at least one cooperating recess for receiving said projection.

7. The system in of claim 1 in which said connector discharge end includes a thread; and said container defines thread for engaging said connector thread so as to connect said container to said connector.

8. The draining system in accordance with claim 1 in which:

said anesthetic agent container includes a neck defining said inlet through which said agent can flow into said container;

said container includes a valve member in said container neck and a first spring in said container neck biasing said valve member to an extended, closed position occluding flow through said inlet; and said connector includes an engaging member engagable with said valve member to move said valve member further into said neck to open said inlet when said container is connected with said connector.

9. The system in accordance with claim 8 in which said container neck has an interior surface defining a valve seat; and said valve member seals against said valve seat to occlude flow into said container when said valve member is in said extended, closed position.

10. A connector for connecting a container to a draining station on an anesthetic vaporizer having a reservoir of a liquid anesthetic agent wherein said draining station has (A) a drain passage communicating between said reservoir on one end and an outlet on the other end and (B) a valve operable to open and close said drain passage, and wherein said container defines an inlet into which said agent can drain, said connector comprising:

a structure having a receiving end for connecting to said draining station at said outlet and having a discharge end for connecting to said container inlet, said structure having a configuration for supporting said container below said draining station outlet so as to preclude any movement of the container with respect to the connector, and said structure defining a transfer passage between said receiving end and said discharge end for draining said agent from said draining station into said container.

11. The connector in accordance with claim 10 in which said connector structure includes relatively movable first and second components.

12. The connector in accordance with claim 11 in which said first and second components are relatively rotatable.

13. The connector in accordance with claim 11 in which said first component includes a rigid conduit member defining an internal transfer passage; and said second component is a generally annular sleeve rotatable on said conduit member.

14. The connector in accordance with claim 13 in which said conduit member defines an external, circumferential groove; and said sleeve includes an inwardly extending flange received in said groove.

15. The connector in accordance with claim 14 in which said sleeve has a generally cylindrical interior wall surface; and a plurality of recesses are defined by said sleeve in said generally cylindrical interior wall surface.

16. The connector in accordance with claim 15 in which said recesses are equally spaced around said generally cylindrical interior wall surface; and each said recess is open at an end of said sleeve for slidably receiving a complementary protuberance on the neck of said container around which said sleeve can be disposed.

17. The connector in accordance with claim 11 in which said first component includes a collecting receptacle.

18. The connector in accordance with claim 17 in which two flanges extend in opposite directions from said first component collecting receptacle at said connector receiving end for being received in complementary slots in said draining station.

19. The connector in accordance with claim 18 in which one of said flanges is thicker than the other of said flanges.

20. The connector in accordance with claim 13 in which said first component includes a rigid conduit member extending from said collecting receptacle and defining a transfer passage communicating with said collecting receptacle.

21. The connector in accordance with claim 20 in which said rigid conduit member has a distal end at said connector discharge end; and said conduit member has an external male thread adjacent said distal end for threadingly engaging a female thread in the neck of said container.

22. The connector in accordance with claim 21 in which said conduit member further has (1) a longitudinal support wall extending across a longitudinal cross section of said transfer passage and extending adjacent said distal end of said first conduit member, and (2) an engaging boss which (a) projects from said support wall for engaging a valve member in a container, and (b) has a size and shape that permits liquid flow out of said transfer passage and around said boss.

23. A draining system for draining a liquid anesthetic agent from a reservoir of an anesthetic vaporizer, said system comprising:

(A) an anesthetic agent container defining an inlet into which said agent can drain;

(B) a draining station on said vaporizer, said draining station having an outlet and defining a drain passage communicating between said vaporizer reservoir on one end and said outlet on the other end, said draining station including a valve operable to open and close said drain passage; and (C) a connector having a receiving end for connecting to said draining station at said outlet and having a discharge end for connecting to said container inlet, said connector defining a transfer passage between said receiving end and said discharge end for draining said agent from said draining station into said container, said connector defines first and second flanges at said receiving end, said draining station defines first and second slots of differing thicknesses for matingly receiving said first and second flanges, respectively; and said slots and flanges define a first mating key configuration.

24. The system of claim 23 in which said flanges have different thicknesses.

25. The system of claim 24 in which said connector includes structure configured to support and maintain said container below said draining station outlet.

26. The system of claim 25 in which said connector and container define second mating structural key configurations.

27. The system of claim 26 in which said container and connector having at least one projection, and the other of said container and connector having at least one cooperating recess for receiving said projection.

28. The system of claim 23 in which said connector includes a collecting receptacle that (1) is disposed between, and connected to, said flanges, (2) defines between said flanges an opening that can be positioned at said draining station outlet adjacent said drain passage, and (3) communicates with said connector transfer passage.

29. A connector for connecting a container to a draining station on an anesthetic vaporizer having a reservoir of a liquid anesthetic agent wherein said draining station has (A) a drain passage communicating between said reservoir on one end and an outlet on the other end and (B) a valve operable to open and close said drain passage, and wherein said container defines an inlet into which said agent can drain, said connector comprising:

a structure having a receiving end for connecting to said draining station at said outlet and having a discharge end for connecting to said container inlet, said connector defines first and second flanges at said receiving end, said draining station defines first and second slots of differing thicknesses for matingly receiving said first and second flanges, respectively; and said slots and flanges define a first mating key configuration.

30. The system of claim 29 in which said flanges have different thicknesses.

31. The system of claim 30 in which said structure having a configuration for supporting said container below said draining station outlet, and said structure defining a transfer passage between said receiving end and said discharge end for draining said agent from said draining station into said container.

* * * * *